United States Patent [19]

Johnston et al.

[11] Patent Number: 5,580,716
[45] Date of Patent: *Dec. 3, 1996

[54] PARASITE-DERIVED RESISTANCE

[75] Inventors: Stephen A. Johnston, 309 N. Gregson, Durham, N.C. 27701; John C. Sanford, Geneva, N.Y.

[73] Assignees: Stephen A. Johnston, Dallas, Tex.; Cornell Research Foundation, Inc., Ithaca, N.Y.; a part interest

[*] Notice: The term of this patent shall not extend beyond the expiration date of Pat. No. 5,240,841.

[21] Appl. No.: 344,616

[22] Filed: Nov. 17, 1994

Related U.S. Application Data

[63] Continuation of Ser. No. 68,168, May 28, 1993, abandoned, which is a continuation of Ser. No. 856,889, Mar. 25, 1992, Pat. No. 5,240,841, which is a continuation of Ser. No. 449,049, Dec. 14, 1989, abandoned, which is a continuation of Ser. No. 842,484, Mar. 21, 1986, abandoned, which is a continuation-in-part of Ser. No. 714,263, Mar. 21, 1985, abandoned.

[51] Int. Cl.$^6$ .............................. C12Q 1/70; C12Q 1/68; C12N 5/14; C12N 15/66
[52] U.S. Cl. .................................. 435/5; 435/6; 435/69.1; 435/172.3; 435/240.1; 435/240.4; 435/252.3; 435/320.1
[58] Field of Search .......................... 514/44; 435/172.3, 435/320.1, 240.1, 240.2, 240.4, 252.33, 69.1, 5, 6

[56] References Cited

FOREIGN PATENT DOCUMENTS

| | | |
|---|---|---|
| 0110385 | 6/1984 | European Pat. Off. . |
| 0140308 | 5/1985 | European Pat. Off. . |
| 0194809 | 9/1986 | European Pat. Off. . |
| 2148302A | 5/1985 | United Kingdom . |
| 83/01451 | 4/1983 | WIPO . |
| 8504898 | 11/1985 | WIPO . |

OTHER PUBLICATIONS

D. Baulcombe et al., "Expression of Biologically Active Viral Satellite RNA from the Nuclear Genome of Transformed Plants", *Nature*, May 1986, 321:446–449.

B. Harrison et al., "Virus Resistance in Transgenic Plants that Express Cucumber Mosaic Virus Satellite RNA", *Nature*, Aug. 1987, 328:799–802.

W. Gerlach et al., "Construction of a Plant Disease Resistance Gene from the Satellite RNA of Tobacco Ringspot Virus ", *Nature*, Aug. 1987, 328:802–805.

T. Frischmuth et al., "African Cassava Mosaic Virus DI DNA Interferes with the Replication of Both Genomic Components", *Virology*, Apr. 22, 1991, 183:539–544.

N. Jacquemond et al., "A Gene Coding for a Monomeric Form of Cucumber Mosaic Virus Satellite RNA Confers Tolerance to CMV", *Molecular Plant–Microbe Interactions*, 1988, 8:311–316.

J. Stanley et al., "Defective Viral DNA Ameliorates Symptoms of Geminivirus Infection in Transgenic Plants", *Proc. Natl. Acad. Sci. USA*, Aug. 1990, 87:6291–6295.

M. Lapidot et al., "A Dysfunctional Movement Protein of Tobacco Mosaic Virus that Partially Modifies the Plasmodesmata and Limits Virus Spread in Transgenic Plants", *The Plant Journal*, 1993, 4:959–970.

S. Blanc et al., "Biological Activity of Cauliflower Mosaic Virus Aphid Transmission Factor Expressed in a Heterologous System", *Virology*, 1993, 192:643–650.

D. MacKenzie et al., "Resistance to Tomato Spotted Wilt Virus Infection in Transgenic Tobacco Expressing the Viral Nucleocapsid Gene", *Molecular Plant–Microbe Interactions*, 1992, 5:34–40.

D. Golemboski et al., "Plants Transformed with a Tobacco Mosaic Virus Nonstructural Gene Sequence are Resistant to the Virus", *Proc. Natl. Acad. Sci. USA*, Aug. 1990, 87:6311–6315.

C. Braun et al., "Expression of Amino–Terminal Portions or Full–Length Viral Replicase Genes in Transgenic Plants Confers Resistance to Potato Virus X Infection", Jun. 1992, *The Plant Cell*, 4:735–744.

J. Anderson et al., "A Defective Replicase Gene Induces Resistance to Cucumber Mosaic Virus in Transgenic Tobacco Plants", Sep. 1992, *Proc. Natl. Acad. Sci. USA*, 89:8759–8763.

S. MacFarlane et al., "Plants Transformed with a Region of the 201–Kilodalton Replicase Gene from Pea Early Browning Virus RNA1 are Resistant to Virus Infection", *Proc. Natl. Acad. Sci. USA*, Jul. 1992, 89:5829–5833.

P. Audy et al., "Replicase–Mediated Resistance to Potato Virus Y in Transgenic Tobacco Plants", *Molecular Plant-Microbe Interactions*, 1994, 7:15–22.

M. Longstaff et al., "Extreme Resistance to Potato Virus X Infection in Plants Expressing a Modified Component of the Putative Viral Replicase", *The EMBO Journal*, 1993, 12:379–386.

Y. Inokuchi et al., "Interference with Viral Infection by Defective RNA Replicase", *Journal of Virology*, Dec. 1987, 61:3948–3949.

(List continued on next page.)

*Primary Examiner*—John L. LeGuyader
*Attorney, Agent, or Firm*—Oblon, Spivak, McClelland, Maier, & Neustadt, P.C.

[57] ABSTRACT

A method for conferring resistance to a parasite to a host of the parasite, which comprises isolating a gene fragment from the parasite and inserting the gene fragment or a DNA or RNA segment substantially homologous to the gene fragment or to a DNA or RNA sequence functionally equivalent to the gene fragment into the host, wherein (1) transcription of the gene fragment or the DNA or RNA segment in the host occurs in an anti-sense direction, (2) the gene fragment or the DNA or RNA segment is expressed as a gene product in the host, wherein the gene product is capable of disrupting an essential activity of the parasite, or (3) the gene fragment or the DNA or RNA segment is a binding site capable of competing with a native binding site in the parasite, is disclosed along with hosts produced by this process. Particularly preferred is conferring resistance using a gene fragment from a replicase gene of an RNA virus.

28 Claims, 1 Drawing Sheet

OTHER PUBLICATIONS

M. Rezaian et al., "Anti–Sense RNAs of Cucumber Mosaic Virus in Transgenic Plants Assessed for Control of the Virus", *Plant Molecular Biology*, Jul. 1988, 11:463–471.

W. Dougherty et al., "RNA–Mediated Virus Resistance in Transgenic Plants: Exploitation of a Cellular Pathway Possibly Involved in RNA Degradation", *Molecular Plant–Microbe Interactions*, 1994, 7:544–552.

J. Lindbo et al., "Untranslatable Transcripts of the Tobacco Etch Virus Coat Protein Gene Sequence Can Interfere with Tobacco Etch Virus Replication in Transgenic Plants and Protoplasts", *Virology*, 1992, 189:725–733.

P. Haan et al., "Characterization of RNA–Mediated Resistance to Tomato Spotted Wilt Virus in Transgenic Tobacco Plants", *Bio/Technology*, Oct. 1992, 10:1133–1137.

R. van der Vlugt et al., "Evidence for Sense RNA–Mediated Protection to $PVY^N$ in Tobacco Plants Transformed with the Viral Coat Protein Cistron", *Plant Molecular Biology*, 1992, 20:631–639.

C. Huntley et al., "Minus Sense Transcripts of Brome Mosaic Virus RNA–3 Intercistronic Region Interfere with Viral Replication", *Virology*, 1993, 192:290–297.

R. Beachy et al., "Coat Protein–Mediated Resistance Against Virus Infection", *Annu. Rev. Phytopathol.*, 1990, 28:451–474.

M. Fitch et al., "Virus Resistant Papaya Plants Derived from Tissues Bombarded with the Coat Protein Gene of Papaya Ringspot Virus", *Bio/Technology*, Nov. 1992, 10:1466–1472.

P. Abel et al., "Delay of Disease Development in Transgenic Plants that Express the Tobacco Mosaic Virus Coat Protein Gene", *Science*, May 1986, 232:738–743.

F. Wilk et al., "Expression of the Potato Leafroll Luteovirus Coat Protein Gene in Transgenic Potato Plants Inhibits Viral Infection", *Plant Molecular Biology*, 1991, 17:431–439.

J. Lindbo et al., "Pathogen–Derived Resistance to a Potyvirus: Immune and Resistant Phenotypes in Transgenic Tobacco Expressing Altered Forms of a Potyvirus Coat Protein Nucleotide Sequence", *Molecular Plant–Microbe Interactions*, 1992, 5:144–153.

M. Cuozzo et al., "Viral Protection in Transgenic Tobacco Plants Expressing the Cucumber Mosaic Virus Coat Protein of its Antisense RNA", *Bio/Technology*, May 1988, 6:549–557.

J. Gielen et al., "Engineered Resistance to Tomato Spotted Wilt Virus, a Negative–Strand RNA Virus", *Bio/Technology*, Dec. 1991, 9:1363–1367.

Nejidat et al., "Transgenic Tobacco Plants Expressing a Coat Protein Gene of Tobacco Mosaic Virus are Resistant to Some Other Tobamoviruses", *Molecular Plant–Microbe Interactions*, 1990, 3:247–251.

P. Dhaese et al., "The temperate B, subtilis phage ø105 genome contains at least two distinct regions encoding superinfection immunity", *Mol. Gen. Genet.*, 1985, 200:490–2.

Y. Inokuchi et al., "Interference with Viral Infection by Defective RNA Replicase", *Journal of Virology*, Dec. 1987, 61:3946–3949.

C. Hill et al., "Cloning Expression, and Sequence Determination of a Bacteriophage Fragment Encoding Bacteriophage Resistance in Lactococcus lactis", *Journal of Bacteriology*, Nov. 1990, 172:6419–6426.

T. Holzmayer et al., "Isolation of dominant negative mutants and inhibitory antisense RNA sequences by expression selection of random DNA fragments", *Nucleic Acids Research*, Jan. 15, 1992, 20:711–717.

S. Kim et al., "Bacteriophage Resistance in Lactococcus lactis ssp. Using Antisense Ribonucleic Acid", *J. Dairy Sci.*, Mar. 6, 1992, 75:1761–1767.

A. Gudkov et al., "Cloning mammalian genes by expression selection of genetic suppressor elements: Association of kinesin with drug resistance and cell immortalization", *Proc. Natl. Acad. Sci. USA*, Apr. 1994, 91:3744–3748.

R. Hull et al., "Approaches to Nonconventional Control of Plant Virus Diseases", *Critical Reviews in Plant Sciences*, 1992, 11(1):17–33.

P. J. M. van den Elzen et al., "Engineering virus resistance in agricultural crops", *Plant Molecular Biology*, 1989, 13:337–346.

Tig, (1985), vol. 1, pp. 22–25, "Anti–Sense RNA As A Molecular Tool For Genetic Analysis", Weintraub Et Al.

Science, (1985), vol. 229, pp. 345–352, "Constitutive And Conditional Suppression Of Exogenous And Endogenous Genes By Anti–Sense RNA", Izant ET al.

Letters To Nature, (1985), vol. 313, pp. 703–706, "Production Of Phenocopies By Krueppel Anti–Sense RNA Injection Into Drosophila Embryos", Rosenbert Et Al.

Molecular And Cellular Biology, (1985), vol. 5, pp. 2341–2348, "Gene Expression From Both Intron–Less And Intron–Containing Rous Sarcoma Virus Clones Is Specifically Inhibited By Anti–Sense RNA", Chang Et Al.

The Journal Of Biological Chemistry, (1985), vol. 260, pp. 9085–9087, "Thermal Regulation Of Beta–Galactosidase Synthesis Using Anti–Sense RNA Directed Against The Coding Portion Of The mRNA", Ellison Et Al.

J. Cell Biol., (1985), vol. 101, pp. 1094–1099, "Translation Of mRNA Injected Into Xenopus Oocytes Is Specifically Inhibited By Antisense RNA", Harland Et Al.

Trends In Biochem Sci., (1985), vol. 10, pp. 232, "Antisense RNA" Nordstroem.

Proc. Japan Acad., (1983), vol. 59, "Regulation Of Gene Expression By A Small RNA Transcript (micRNA) In *Excherichia Coli* K–12", Mizuno Et Al.

Cell, (1985), vol. 42, pp. 129–138, "Stable Reduction Of Thymidine Kinase Activity In Cells Expressing High Levels Of Anti–Sense RNA", Kim Et Al.

Proc. Natl. Acad. Sci, (1985), vol. 82, pp. 144–148, "Injected Anti–Sense RNAS Specifically Block Messenger RNA Translation In Vivo", Melton.

J. Theor. Biol. (1985), vol. 113, pp. 395–405, "The Concept Of Parasite–Derived Resistance—Deriving Resistance Genes From The Parasite's Own Genome", Sanford Et Al.

Proc. Natl. Acad. Sci, (1978), vol. 75, pp. 285–288, "Inhibition Of Rous Sarcoma Viral RNA Translation By A Specific Oligodeoxyribonucleotide", Stephenson Et Al.

Proc. Natl. Acad. Sci, (1978), vol. 75, pp. 280–284, "Inhibition Of Rous Sarcoma Virus Replication And Cell Transformation By A Specific Oligodeoxynucleotide", Zamecnik Et Al.

Biological Abstracts, (1985), vol. 80, Genetics Of Bacteria And Viruses.

Bio/Technology, (1986), vol. 4, "A New Route To Virus Resistance In Plants", Bialy Et Al.

Plant—Microbe Interactions, (1984), pp. 420–429, "A Model To Explain The 'Cross–Protection' Phenomen Shown By Plant Viruses And Viroids", Palukaitis Et Al.

PARASITE-DERIVED RESISTANCE

This application is a continuation of application Ser. No. 08/068,168, filed on May 28, 1993, now abandoned, which is a continuation of application Ser. No. 07/856,889, filed on Mar. 25, 1992 (now U.S. Pat. No. 5,240,841), which is a continuation of application Ser. No. 07/449,049, filed on Dec. 14, 1989, now abandoned, which is a continuation of application Ser. No. 06/842,484, filed on Mar. 21, 1986, now abandoned, which is a continuation-in-part of application Ser. No. 06/714,263, filed on Mar. 21, 1985, now abandoned.

BACKGROUND OF THE INVENTION

1. Field of the Invention

The present invention relates to methods of conferring resistance to parasites, such as viruses, bacteria, and higher parasites, to hosts of the parasite. More particularly, the present invention relates to vital resistance obtained by genetic engineering of the host organism to contain a portion of a replicase enzyme from an RNA virus.

2. Description of the Background

A potentially important application of genetic engineering technology is in the area of producing resistance to parasites. The proposals in the prior art that have been systematic and broadly applicable have centered on finding a gene conferring resistance within a strain of the host species or within a related species and transforming the gene into the genome of a susceptible host. This approach may prove effective but has several distinct disadvantages. Resistant forms of the host may not exist or may be very difficult to find for each new race of parasite which arises. Such resistance may be polygenic, making the cloning and transfer of the resistance genes difficult. Where resistance is encoded by a gene, there are commonly already strains of the parasite that have evolved virulence genes for overcoming such host-derived resistances in a gene-for-gene fashion (Flor 1971). Finally, the problem of identifying and isolating the resistance gene from within the large genome of the host will generally remain very difficult. An alternative strategy that addresses these problems is therefore needed.

There have also been proposals for and some work on using genes from organisms unrelated to either host or parasite, which serendipitously have gene products detrimental to a specific parasite. The gene coding for the endotoxin of *Baccillus thuringliensis* (which is toxic to *lepidopterous* insects) would be an example of this (Held et al., 1982). While this type of approach may prove useful in some specific cases, it clearly represents an opportunistic approach to the problem, as opposed to a systematic methodology that can be applied very broadly.

There already exist some examples of .genes, gene derivatives, or gene products of a parasite that can produce a negative interaction with itself or a related genotype. Studies into the susceptibility of plants to infection by viruses have demonstrated that closely related plant viruses or different strains of the same virus will cross-protect a host organism (Hamilton, 1980). In other words, a plant infected by a first virus is often not subject to infection by a second strain of that virus or by a related virus. A similar phenomenon has been observed in animal viruses and has been termed intrinsic interference (Marcus and Carrier, 1967). From the point of view of parasite resistance of the type discussed herein, the key proteins involved in the intrinsic interference phenomenon are the viral replicase proteins (Marcus and Zuckerbraun, 1970). These same authors proposed that the replicase proteins of the primary infecting virus prevent the replication of the second virus by binding to its replicase attachment sites (Marcus and Zuckerbraun, 1969). A similar proposal has been put forth to explain cross-protection in plants (Gibbs, 1969). In a similar manner, experimenters working with an *E. coli* infected with bacteriaphage 434 have found that infected bacteria are immune to other phages (Lauer et al, 1981; Flashman, 1978; Roberts et al, 1979). Other workers have noticed that endogenous as well as experimentally introduced complementary oligonucleotides can interact with mRNA in a potentially detrimental manner. Simons and coworkers (1983) have suggested that hybridization of a small anti-sense transcript to *E. coli* Tn10 mRNA contributes to the regulation of transposition of that element. Stephenson and Zamecnik (1978) and Zamecnik and Stephenson (1978) have shown that synthetic oligodeoxynucleotides, complementary to Rous sarcoma virus terminal repeats, diminish normal viral infection and can inhibit viral RNA translation in vitro. However, these discoveries were not applied to the production of host resistance to a parasite.

Despite this fragmentary knowledge in the prior art, there still remains a need for a fully developed technique for producing resistance to parasites that is not based on the traditional methods of using a resistance gene from an immune strain of a host.

SUMMARY OF THE INVENTION

According, it is an object of this invention to provide a method of conferring resistance to a parasite (specifically an RNA virus) to a host of the parasite which does not rely on the necessity of identifying and isolating a resistance gene from an immune strain of the host.

This and other objects of the invention as will hereinafter become more readily apparent have been accomplished by providing a method for conferring resistance to a parasite to a host of said parasite, which comprises isolating a gene fragment from an RNA virus, wherein the gene from which said gene fragment is derived codes for a replicase enzyme, and inserting said gene fragment or a DNA segment substantially homologous to at least a part of said gene fragment into said host, wherein said gene fragment or DNA segment is expressed as a peptide in said host, wherein said peptide is capable of binding to a replicase binding site in said host.

BRIEF DESCRIPTION OF THE DRAWING

The FIGURE shows in schematic form the replicase gene from Qβ and its cleavage sites as described in detail in this application as well as the location of the replicase insert in plasmid pUC18.

DESCRIPTION OF THE PREFERRED EMBODIMENTS

Figure 1:
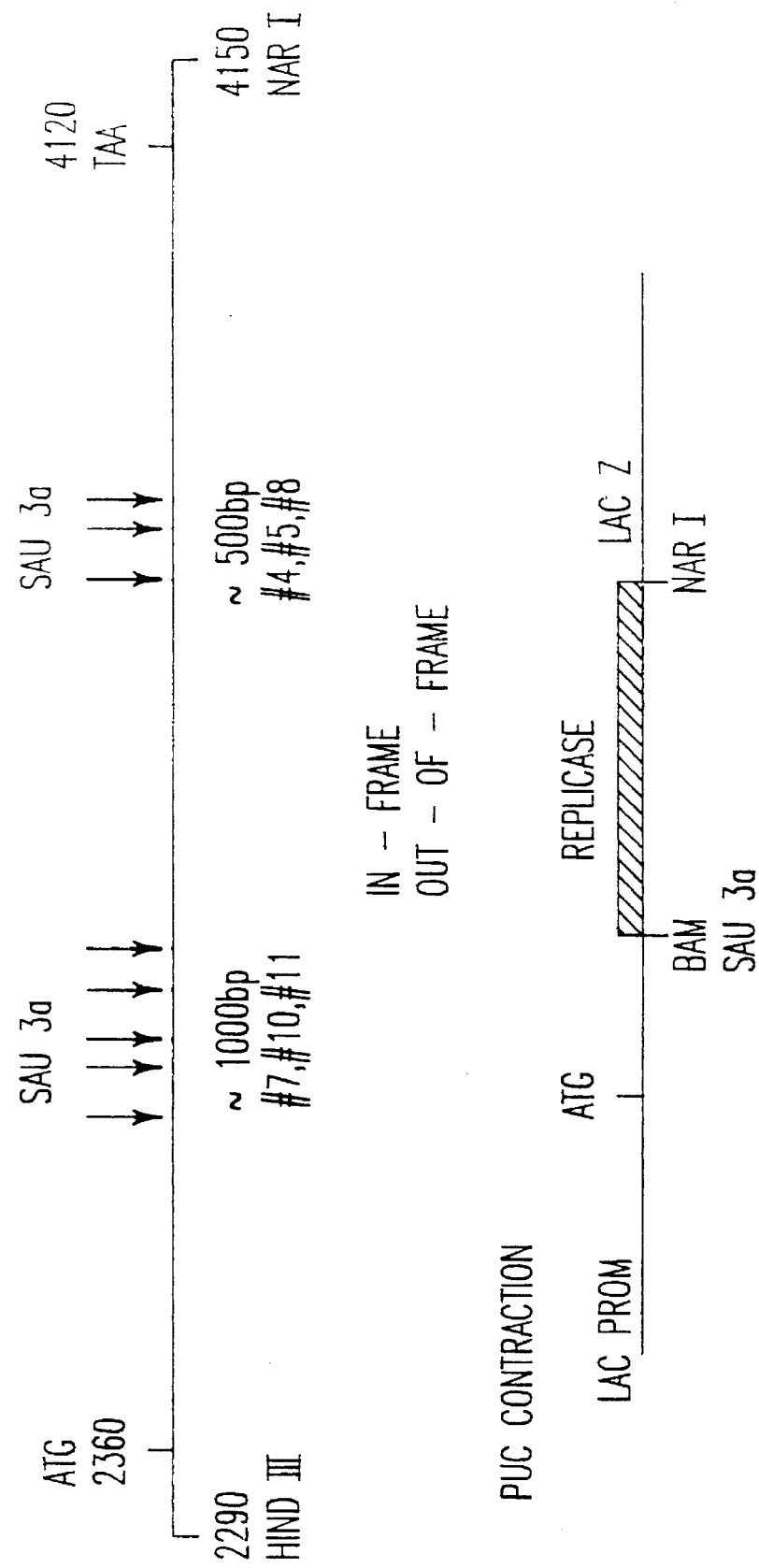

The concept off parasite-derived resistance is that host resistance to a particular parasite can effectively be engineered by introducing a gene, gene fragment, or modified gene or gene fragment of the pathogen into the host. This approach is based upon the fact that in any parasite-host interaction, there are certain parasite-encoded cellular functions (activities) that are essential to the parasite but not to the host. An essential function is one which must operate if the parasite is to survive or reproduce. These functions represent the Achilles heel of the parasite. If one of these functions is disrupted, the parasitic process will be stopped.

"Disruption" refers to any change that diminishes the survival, reproduction, or infectivity of the parasite. Such essential functions, which are under the control of the parasite's genes, can be disrupted by the presence of a corresponding gene product in the host which is (1) dysfunctional, (2) in excess, or (3) appears in the wrong context or at the wrong developmental stage in the parasite's life cycle. If such faulty signals are designed specifically for parasitic cell functions, they will have little effect on the host. Therefore, resistance to a particular pathogen can be achieved by cloning the appropriate parasite gene, if necessary modifying its expression, and transforming it into the host genome. By resistance is meant any reduction in virulence of the parasitic infection or any reduction in the susceptibility of the host to the parasite.

This approach to engineering resistance has important advantages:

1) The source of resistance genes would never be in question, since each parasite would bring with it the genes necessary for deriving resistance.

2) The stability of parasite-derived resistance will generally be greater than the stability of simply inherited forms of host resistance, for reasons that are discussed later in more detail.

3) The difficulties involved in cloning genes from host organisms, which generally have larger genomes relative to their pathogens, are lessened.

4) Parasite-derived resistance will have a minimal effect on the host and should not produce substances harmful to man.

The general concept of parasite-derived resistance is described in U.S. patent application Ser. No. 714,263, filed Mar. 21, 1985, which is herein incorporated by reference. The inventors have now specifically reduced to practice a particular embodiment of the invention described generally in the parent application. As will be described in detail later, the specific embodiment is related to the replicase gene of an RNA virus.

All positive-strand RNA viruses that have been investigated contain an enzyme known as RNA replicase, which can utilize vital RNA as the template for the formation of new RNA. RNA replicase is not normally present in a host cell, but is produced when the cell is infected with an RNA virus.

Vital RNA codes for formation of an RNA replicase which functions only with viral RNA as a template and ignores all other RNA molecules. Accordingly, the RNA replicase represents a vital function that is not mart of a normal host function and thereby represents a preferred means of conferring resistance to a host using genes derived from the parasite (vital) organism.

Since replicase enzymes in both plant and animal RNA viruses have striking sequence and functional similarities, the present invention allows the production of resistance to a wide variety of RNA viruses in a simple and straightforward manner. It is possible to use either the specific replicase domain (peptide resulting from a gene fragment as described herein) to confer resistance to other RNA viruses, or equally possible to select from other viruses domains having functional homology for the domain of the Qβ virus used in the current reduction to practice.

The present invention is practiced by isolating a gene fragment from the replicase gene of an RNA virus, preferably Qβ virus, and inserting the gene fragment or a DNA or RNA segment substantially homologous to at least a part of the gene fragment or to a DNA or RNA sequence substantially equivalent to the gene fragment into the host, whereby the gene fragment or DNA or RNA segment is expressed as a gene product (peptide) in the host. In particular, a gene fragment is selected which produces a peptide containing the binding region (for RNA) of the replicase enzyme. When the gene product, which is less than the entire replicase enzyme and therefore is not capable of functioning as a replicase enzyme, binds to the RNA, it prevents binding of an active replicase enzyme and therefore protects the host against the results of infection by an active virus.

The present reduction to practice was obtained using a gene fragment from the Qβ virus and is therefore a preferred embodiment of the invention. However, gene fragments from the replicase gene of other RNA viruses are equally usable in the method of the present invention.

When a Qβ replicase gene fragment is used, it is preferred to obtain this fragment by cleaving Qβ replicase cDNA with Sau3a at the 5' terminal of the fragment and with NarI at the 3' terminal of the fragment. Use of these designated restriction enzymes produces fragments of the replicase gene of two types, approximately 500 and approximately 1,000 base pairs in length. There are a number of spaced Sau3a cleavage sites in the replicase gene closely spaced from one another so that there are at least five fragments of approximately 1000 base pairs in length and at least three fragments of approximately 500 base pairs in length, all terminating at a NarI cleavage site. The NarI site is beyond the transcriptional termination site of the replicase gene.

It is preferred to prepare a DNA vector by annealing a 5' Sau3a site in the replicase coding region to a BamHI site in the lacZ gene on the plasmid pUC18. This creates a gene, when in-frame, encoding a few amino-terminal amino acids of lacZ followed by a replicase protein domain of varying sizes (depending on the specific Sau3a cleavage sites selected) which terminates with a NarI site beyond the transcriptional termination site of the replicase gene. The production of the replicase domain would then be under the lacZ promoter control. Some of the Sau3a sites will produce an out-of-frame fusion of replicase, but such inoperable gene products are outside the scope of the present invention and can be readily detected since transformation with a vector containing such gene products would not protect the host against infection with an RNA virus.

In addition to the specific vector described above, it is possible to use gene fragments and DNA segments coding for a peptide capable of duplicating the binding function of the replicase enzyme using standard techniques of genetic engineering and other vectors.

In addition to gene fragments obtained from natural sources of RNA replicase enzymes, it is also possible to practice the method of the present invention using a DNA segment encoding a peptide substantially homologous to a peptide encoded by the transcribed portion of the 3' end of an RNA replicase gene. Substantial homology preferably means at least 90% of the amino acids in a given segment are identical (and preferably that any substitutions are conservative substitutions), more preferably that no more than two (preferably conservative) amino acids within a given segment are different, and most preferably no more than one (preferably conservative) amino acid within a given segment is different.

It is preferred that a DNA segment coding for such a homologous peptide or for a segment of a natural replicase enzyme contains from 400–1200 base pairs (measured by the 3' end of the transcribed portion of an RNA replicase gene), preferably from 500–1000 base pairs in length.

As an example of how disease resistance in general can be engineered by the general approach, the discussion below sets forth in detail how the genes of the bacteriophage Qβ can be used to make *E. coli* resistant to Qβ infection. This example is not to be considered limiting of the invention but is an example of the ease with which the invention can be practiced, now that it is disclosed.

The biology of Qβ and other RNA phages has been extensively documented (Zinder, 1975), and the cDNA sequence of its genome has been determined. The Qβ genome has three major cistrons. These code for a maturation protein (involved in lysis and phage binding to host pili), a coat protein, and a subunit of the replicase enzyme. (A fourth gene product is a minor coat protein which is a read-through product of the coat cistron.

The life cycle of Qβ is basically as follows. The phage begins by binding to the sex pili of F' *E. coli*, through which it enters the cell and begins to translate its replicase subunit. Its replicase subunit polymerizes with three host subunits normally involved in host protein translation. The resulting hybrid tetrameric enzyme has RNA replicase activity specific for Qβ. This specificity is due to the affinity between the Qβ subunit of the tetrameric replicase and a short segment of the Qβ genome within the replicase cistron, The replicase attaches to Qβ RNA at this binding site and replicates the viral RNA. Late in the life cycle of Qβ, coat protein and maturation protein accumulate in the host. The coat protein then binds to the replicase cistron and thereby represses translation of the replicase subunit. Termination of replication allows viral assembly, and eventually the maturation protein lyses the host, releasing a new population of infective Qβ.

From a conventional (prior art) perspective, the life cycle of Qβ suggests two potential mechanisms for developing resistance. Host-derived resistance might be developed by (1) blocking Qβ binding to sex pili or (2) producing variant host subunits lacking affinity for the Qβ replicase subunit. Blocking Qβ binding is, in fact, a known mechanism for producing Qβ resistance, since non-F' routants lacking pili are immune to infection (Silverman, Rosenthal, Mobach and Valentine, 1968) However, this strategy clearly disrupts a mechanism which is relevant to the host's fitness as a species. The selection of variant forms of the host subunits which help make up the replicase enzyme may also be a naturally occurring mechanism conferring resistance. Since the host supplies 3 of the 4 subunits of the viral replicase, one might expect mutations within these genes to confer resistance. However, the extent to which these host subunits can be altered is clearly limited, since these subunits are essential to host protein synthesis and the survival of the host. Most of the variants of these host subunits would probably be lethal or sub-lethal for the host. Even non-lethal variants are likely to be suboptimal for protein translation efficiency. Therefore, both of the host-derived resistance mechanisms suggested by the Qβ life cycle would be obtained at the expense of disrupting crucial host functions.

The prospect of being able to transfer genes from parasite to host provides a new approach to resistance. Viewed from this perspective, the life cycle of Qβ suggests at least as many mechanisms of pathogen-derived resistance as host-derived resistance. Several strategies are seen to be promising: (1) deriving resistance from the Qβ coat protein; (2) deriving resistance from a modified Qβ replicase; (3) deriving resistance by cloning the Qβ replicase binding site, and (4) deriving resistance from expression of anti-sense strand RNA sequences. Another strategy involving the maturation protein also appears feasible.

Resistance Derived from the Coat Protein

Qβ coat protein is known to have a regulatory, as well as a structural role. Late in the phage life cycle, coat protein binds to and represses the cistron coding for the Qβ replicase subunit, stopping replication and allowing vital assembly (Bernardi and Spahr, 1972). When cDNA to the coat protein translational sequence is linked to an *E. coli* promoter and introduced into *E. coli*, the coat protein is produced in the host. Expression of coat protein (in sufficient quantity) in the host will repress replication of any infecting Qβ, thereby conferring resistance on the transformed host.

Resistance Derived from a Derivative of the Replicase Gene

The Qβ replicase subunit has a dual affinity for a segment of the Qβ genome and the three host replicase subunits (Kamen, 1970; Meyer, Webster and Weissmann, 1981). If the Qβ replicase gene is cloned (as cDNA) and mutagenized, some variant forms will be able to bind to the Qβ replicase site and at the same time fail to polymerize with the host subunits, a requirement to form a functional replicase. Alternatively, a portion of the replicase gene can be cloned to produce a polypeptide containing the functional domain for binding the replicase site but incapable of interacting with the host subunits. A transformed host producing such a modified replicase subunit would be Qβ-resistant if the modified Qβ replicase subunit or a portion of it binds to the replication sites of infecting Qβ and effectively competes with native Qβ replicase for binding sites, thus disrupting Qβ replication. Details of this strategy are set forth in other locations of this specification.

Resistance Derived from Cloned Replicase Binding-Site

The above-mentioned replicase binds to a specific segment of the Qβ genome which is roughly 100 base pairs in length. If this segment is cloned (cDNA) and introduced into the host, it would be transcribed constitutively as mRNA if attached to an appropriate promoter. The transformed host would then be resistant to Qβ because the binding site, which has been shown to compete for binding of the replicase enzyme in vitro (Meyer, Weber and Weissmann, 1976), would limit the free replicase available for Qβ replication.

Anti-sense Strand Interference

The presence of an RNA complementary to Qβ RNA would allow formation of an RNA—RNA duplex that would block Qβ infection. This can be accomplished, for example, by transcribing a cDNA clone of a portion of Qβ in the reverse orientation in the *E. coli* host. The anti-sense strand RNA produced will then hybridize to the infecting Qβ and interlet with its proper translation or packaging. The advantages of this approach are that potentially any fragment of the vital genome could be used without modification, and it would be extremely difficult for the virus to overcome this form of resistance.

Resistance Derived from Qβ Maturation Protein

Although the maturation protein's mode of action is not yet well understood (Karik and Billeter, 1983; Winter and Gold, 1983), it also represents a potential source of pathogen-derived resistance. A modified maturation protein in the host can block lysis. Alternatively, a repressed operon containing a wild-type maturation gene can be engineered in the host that would be activated by Qβ infection. This would induce premature lysis of a host cell upon initial infection by Qβ, constituting (on the population level) a form of hypersensitivity.

Although the examples set forth above describing methods by which bacteria can be protected from bacteria phage Qβ are related in particular to a specific host/parasite system, the techniques are readily applicable to other systems, such as the protection of other organisms from both viral and non-viral infections. Techniques for achieving these results are set forth in more detail in the following paragraphs.

Virus Resistance

The most likely early application of the concept of parasite-derived resistance is in engineering virus resistance. This is because the vital genome is small, and, since virus only propagates in the host, most of the genome is involved in pathenogenicity. Portions of the vital genome can be cloned and their potential for conferring resistance readily determined. Alternatively, resistance-conferring genes can be discovered empirically by testing the biological effect of various DNA restriction fragments of the vital genome. Most virus-derived resistances are likely to involve a block in replication. The methods described for engineering resistance to Qβ are directly applicable to any virus which a) codes for a protein which helps regulate the virus' reproduction; b) has specific binding sites in its genome; c) synthesizes its own replicase or reverse transcriptase; or d) is bound by complementary reverse strand sequences of nucleic acid. In other words, these methods would apply to essentially all viruses.

While there has been some controversy among biochemists regarding whether plant viruses encode their own replicase, it now seems likely that most plant viruses do code for all or part of their replicases (Hall, Miller and Bujarski, 1982; Dorssers, Van der Meer, Kamen, Zabel, 1983). The first plant virus to have its replication mechanism characterized, turnip yellows mosaic virus, has proven analogous to Qβ (Mouches, Candresse and Bove, 1984). This virus has been shown to have a hybrid replicase, with its own sub-unit conferring specific binding to its genome. This indicates that the approach described for Qβ replicase would also apply to this virus. It is likely that most or all RNA plant viruses will code either for their own replicase, a subunit of the replicase, or a protein modifying the specificity of the host's RNA polymerase. It is known that there is substantial homology between replicases from a wide variety of RNA variety of RNA viruses (Kamen and Argos, 1984). This means that the replicase-derived resistance strategy outlined for Qβ will be directly applicable to a wide range of plant viruses. Many viruses have not yet been analyzed relative to this genetic structure. However, the very small size of the vital genome and the diversity of potential resistance mechanisms clearly indicates that a vital-derived resistance gene can be derived from any virus simply by using standard shotgun cloning methods and direct screening for subsequent resistance to the virus.

Non-vital Resistance

The application of parasite-derived resistance to extracellular parasites is more complex than for vital parasites. Since false signals coded for by the host must be recognized by the parasite, parasite-derived resistance will only be useful where mechanisms exist which allow recognition or incorporation by the parasite of non-degraded macromolecules from the host. Van der Plank (1978) has offered persuasive theoretical arguments indicating that such an exchange of macromolecules between the host and the parasite often occurs. There is at least one case where such incorporation has been documented. In the malaria host/parasite system the parasite has been shown to incorporate and utilize a host dismutase enzyme, indicating the presence of a protein exchange mechanism (Fairfield, Meshnick and Eaton, 1983). To the extent that such mechanisms exist in other non-viral host/parasite relationships, the techniques described herein can be applied without significant modification. The existence of protein exchange mechanisms can be determined using monoclonal antibody probes to locate sub-cellular components, in conjunction with 2-D electrophoretic studies searching for host-parasite hybrid proteins.

Given a macromolecular exchange mechanism, a variety of approaches to the engineering of parasite-derived resistance exist for either vital or non-vital parasites. For example, in gene-for-gene host/parasite systems (Flor, 1971; common in vital, fungal, and bacterial pathogens), it is generally found that the parasite's avirulence alleles are dominant to virulence alleles (reviewed in Van der Plank, 1978). This suggests that the avirulence gene products override or block the activity of the virulence gene products—thereby preventing infection. Thus, an avirulence allele cloned from an avirulent strain of the parasite, when introduced and expressed constitutively in a transformed host, can enter the parasite or act at the host-parasite interface and override the infective capacity of an otherwise virulent pathogen. Avirulence alleles can be identified by a variety of methods. For example, in bacteria the virulence-avirulence locus can be cloned by using insertional mutation (employing transposable elements) of the virulent strain and screening for non-virulent mutants or by screening a genomic library for complementation of the virulence allele. The virulence gene can then be introduced into the host to confer resistance. Recently, an avirulence gene has been cloned from the bacterial pathogen *Pseudomonas syringae.* However, the expressed intent of these workers is to clone the resistance gene from the host and the parasite gene has not been introduced into the host in any form (Staskawicz et al 1984). The technique proposed here introduces an entirely new dimension to the classical model of gene-for-gene host/parasite interactions.

Resistance from the Parasite's Regulatory Genes

A more general strategy for engineering parasite-derived resistance (applicable with or without gene-for-gene interactions) utilizes specific regulatory genes from the parasite. For example, fungal genes regulating haustorial development or sporulation can be introduced into a host, thereby disrupting the normal life cycle of the fungal pathogen, using established techniques of identifying the regulatory protein and searching a genomic library with an antibody probe. Once cloned, such genes can be introduced into a host, where they will disrupt the normal life cycle of the fungal pathogen. This type of regulatory approach appears particularly useful in the engineering of insect resistance. For example, all insects depend on the regulated biosynthesis of juvenile and molting hormones for precise timing of molting, metamorphosis and reproduction. Using the techniques of this invention, it is possible to incorporate into the host genes from the insect pest encoding the activities necessary to produce the insects' hormones, pheromones or neurotransmitters. In the case of neurotransmitters, these polypeptides are typically extremely short (less than 20 amino acids) and are therefore easily sequenced, and artificial genes coding for these sequences can then be synthesized de novo. In the case of non-peptide hormones or pheromones the problem is more difficult but can be overcome. Typically, several enzymatic steps will be required from the starting point of a common precursor in both host and parasite to the biologically active secondary metabolite. This means that several genes in the parasite will have to be identified, cloned and transferred to the host. While this approach does not have the simplicity or directness of other parasite-derived approaches, it is potentially one of the more significant and broad-spectrum applications of parasite-derived resistance, and will generally warrant the time and expense of engineering the latter part of a biosynthetic pathway. The host producing such insect growth regulators or transmitters would be resistant by virtue of disrupting the behavior or life cycle of the insect pathogen, thereby eliminating infection of the primary host. There are examples in nature where plants seemed to have exploited a similar strategy for resistance by evolving genes producing analogs to, or biosynthetic antagonists of, insect hormones (Bowers, 1980).

Another application of parasite-derived resistance is available where an insect or other organism serves as an intermediate host, so that the disease cycle can be disrupted by making the intermediate host resistant to the pathogen, thereby eliminating infection of the primary host. For example, efforts to control malaria have previously focused on eradication of the intermediate host, the Anopheles mosquito. If however, genes from the Plasmodium pathogen are introduced into the mosquito in a manner to confer resistance by disrupting the life cycle of the parasite, the disease cycle will be broken. This approach is most feasible if the resistance genes is of selective advantage to the intermediate host, allowing resistance genes to be maintained and propagated in natural populations after introduction of modified individuals. This can be done, for example, by concurrently introducing resistance to a pesticide into the intermediate host.

Advantages and Limits of Pathogen-derived Resistance

Parasite-derived resistance represents a systematic and broadly-relevant approach to the problem of how to genetically engineer insect and disease resistance. The rich possibilities of this approach are illustrated by the fact that three different strategies for deriving resistance from the Qβ bacteriophage exist in a parasite having only three genes. There are several distinct advantages of parasite-derived resistance.

One of the most attractive features of parasite-derived resistance is that each new parasite or race of parasite that becomes a problem simultaneously brings with it the specific genes needed to engineer resistance to itself. These genes can be systematically identified within the parasite's genome. Once such genes have been identified, homologous genes in other parasite races or in related parasites will be readily identifiable by DNA hybridization techniques. This eliminates the need for repeated and exhaustive searches through the host's germplasm pools, seeking rare host resistance genes.

Another major advantage of this strategy is that it should not generally be disruptive of host functions. Van der Plank (1978), using evolutionary arguments and population genetics data, has argued that host genes controlling susceptibility exist because they involve essential host functions. Most hosts are genetically susceptible because the susceptible allele is optimal relative to its natural function. Host-derived resistance alleles, therefore, tend to disrupt the optimal functioning of the host. To the extent that this is true, most host-derived resistances attack the pathogen indirectly by replacing an optimal host gene product with a non-optimal host gene product which happens to be incompatible with the parasite. This is seen in the Qβ system, where host-derived resistance is likely to be achieved either by disrupting sex pili formation or by tampering with the host's protein-synthesis machinery. A similar situation exists with sickle-cell anemia, which is harmful to humans when expressed but which confers resistance to malaria in persons who have both a recessive sickle-cell gene and a normal hemoglobin gene. The beauty of the concept of pathogen-derived resistance is that only pathogenic cell functions are attacked and are attacked directly, which will have minimal subsequent effect on the host. The specificity of parasite-derived resistance is not only desirable in terms of being non-disruptive to the host, but also of being non-harmful to man. Resistance based upon production of general toxicants, such as the natural pesticides of many resistant plant taxa, have been shown to be potentially harmful to man when ingested (Ames, 1983). The specificity of parasite-derived resistance should preclude, to a large extent, any such harm to man.

There are reasons to believe that parasite-derived resistance should be relatively durable compared to host-derived resistance. The ability of parasites to circumvent host-generated general toxicants is well known. Additionally, specific host-derived resistance genes are frequently overcome by matching gene-for-gene mutations to virulence in the parasite (Flor, 1971). In the case of host-derived Qβ resistance, alterations in the host replicase sub-units (making them incompatible with the viral subunit, thereby conferring resistance), are easily matched by mutations in the Qβ replicase subunit which restore subunit compatability, constituting a mutation to virulence. However, such gene-for-gene mutations circumventing resistance should be relatively rare in the case of parasite-derived resistance. In this case the parasite would usually be facing a new form of resistance, which it had not previously faced in its evolution. These types of resistances are likely to be very difficult for the parasite to overcome, especially where regulatory genes are involved. For example, resistance to Qβ was derived from the Qβ coat protein gene, a new virulent Qβ strain could only arise by first having a new binding site develop by mutation in the replicase cistron (without disrupting replicase function) which would not bind the native coat protein. Simultaneously a new coat protein would have to arise by mutation (without disrupting coat protein function) which would bind to the new binding site. Such a simultaneous and complementary set of mutations (which preserved both coat and replicase functions) should be extremely rare.

Last, engineering parasite-derived resistance should be considerably more approachable on the molecular level than engineering host-derived resistance. There are numerous reasons for this: (1) this strategy would generally focus on the molecular biology of relatively simple organisms with short life cycles; (2) it would generally require only the identification and isolation of individual genes from small genomes; (3) unregulated, constitutive expression of the parasite-derived resistance genes would usually be effective; and (4) it would avoid the complex, multigenic biosynthetic pathways which are the likely basis of many existing host-derived resistances.

There do not seem to be any obvious disadvantages to the parasite-derived approach to resistance, except that application of the strategy to non-virus parasites is only possible where mechanisms exist for macromolecular exchange between host and parasite. Most forms of parasitism, especially those forms displaying gene-for-gene resistance, allow ample opportunity for gene-product interactions and will be suitable for engineering parasite-derived resistance.

Techniques for the Production of Resistant Host

As will be readily understood that those of ordinary skill in the art of genetic engineering, standard techniques of genetic engineering can readily be adopted to attain the goals set forth herein. Protection of a host against a virus, for example, can easily be achieved. Because of the reasons set forth above, it is not necessary to identify the gene being inserted into the host, although identification of the gene will make application of the method easier to perform. In general, genetic information (DNA or RNA) from any virus is isolated using standard procedures and cleaved into pieces of varying lengths, preferably containing at least 20 nucleotides if the DNA is to be transcribed in an anti-sense direction, or at least a functional portion and preferably an entire gene if the gene is to be expressed. DNA fragments are typically obtained using restriction endonuclease enzymes. The same enzyme (or enzymes) is then used to cleave a vector capable of replicating in the host or inserting into a host's chromosome. The vector can be a natural plasmid or transposon or any part thereof capable of replication in the host and, when desired, production of a gene product from the exogenous parasite gene fragment. Vectors derived from plasmids and other vectors normally present in the host are preferred. The viral DNA is inserted into the vector using standard techniques in either a sense direction (when expression of a gene product is desired) or an anti-sense direction. Proper tailoring of the gene fragment in the vector (e.g., employing appropriate 5' and 3' flanking sequences to ensure regulation, transcription, and translation as desired) is readily achieved using standard techniques, especially when simple constitutive expression is desired, as is suitable in most cases of parasite-derived resistance. As used in this application, the phrase "gene fragment" encompasses both entire genes, DNA segments that contain an entire gene or a portion thereof, and segments of DNA that are incomplete parts of a single gene. The word "gene" encompasses both DNA sequences that code for a peptide gene product and other DNA sequences that form a functional part of a chromosome or plasmid.

Although this specification generally refers to DNA alone when describing genetic information, vectors, or the like, this is done for ease of expression only. Any reference to DNA, unless clearly restricted to DNA and not to RNA, is equally applicable to RNA. For example, pathogenic RNA viruses can be the source of the parasite gene fragment, and non-virulent RNA viruses can act as vectors. In many instances, however, it is easier to work with DNA than RNA (e.g., more DNA restriction endonuclease enzymes are known), and use of cDNA prepared from RNA is a preferred embodiment of the invention when producing resistance to an RNA virus.

After a gene fragment has been isolated, the DNA sequence can be determined and modified, if desired, to produce similar DNA segments capable of being expressed as the same or similar gene products. For example, one or more codons can be replaced by equivalent codons to produce artificial DNA segments coding for the identical gene product. Alternately, a codon can be replaced by a codon that codes for a similar amino acid (e.g., a codon for lucine replaced by a codon for isoleucine or a codon for glutamic acid replaced by a codon for aspartic acid). When used as an antisense strand or binding site, less than 10% non-identical nucleotides are preferred with unmodified gene fragments being most preferred. Greater modification of the gene fragment is possible when a gene product of the parasite gene is being produced. For example, artificial DNA sequences containing a series of codons functionally equivalent (i.e., that code for the same amino acids) to the codon sequence in the parasite gene fragment are considered fully equivalent to the parasite gene fragment since they will produce the same gene product, even though the DNA sequence can be substantially different. Gene products not identical to the natural gene product but retaining the ability to produce a gene product capable of disrupting an essential activity of the parasite can be produced by systematic modification of codons (and thus the expressed gene products) followed by testing for parasite resistance. Such modified DNA segments must be substantially homologous to at least a part of the isolated gene fragment or a DNA sequence functionally equivalent thereto in order to be considered indicative of parasite-derived resistance. By "substantial homology" is meant at least 80%, preferably at least 90%, and most preferably at least 95% identity between the DNA sequence in question and the sequence to which it is being compared. Identical sequences are also covered by the same phrase. Comparisons for the purpose of determining homology are preferably made over a sequence of at least 15 and more preferably at least 21 nucleotides.

The phrase "isolating a gene fragment", as used in this application, refers to the process of obtaining a gene fragment to be used in the production of resistance in a useful form. The gene fragment does not have to be purified or otherwise separated from other cellular components, although this will occur in many processes. Instead, the word "isolated" is used to indicate that a gene has been obtained in a useful form by a deliberate process. For example, an "isolated gene fragment" can exist in a mixture of fragments from the DNA of a parasite that is to be used in a shotgun cloning procedure. A gene fragment is also still "isolated" when it is present in the form of a recombinant plasmid present in a bacterium being used in a shotgun cloning procedure to identify producers of desired parasite gene products (such as by use of monoclonal antibodies). Likewise, a segment of purified DNA comprising a parasite gene segment termini from a cloning vector (e.g., obtained by cloning a parasite gene fragment in a bacterial plasmid prior to insertion into the final host) is also encompassed by this term. Other usable forms of gene fragments will be readily apparent to those skilled in genetic engineering.

Insertion of the parasite gene fragment into a host is readily achieved when the host is a bacterium or other unicellular organism since the major advances that have occurred recently in genetic engineering have generally involved insertion of vectors containing exogenous genes into unicellular hosts (especially bacteria and yeasts) and are directly applicable to the present method. "Insertion" encompasses any means of introducing genetic information into a host organism compatible with the limitations discussed in this specification. However, insertion in a manner to provide a heritable characteristic is preferred. In unicellar organisms this can readily be accomplished using heritable plasmids or by insertion of the parasite gene fragment into the host chromosome. These examples are not limiting, and other methods of inserting heritable genetic information, whether into unicellar or higher organisms, are equally applicable to the practice of this invention.

Proven methods for inserting new genes into higher organisms can now be found in a massive volume of current literature. There exist four basic methods of doing this (Baserga, Crose, and Povera, Eds., 1980): (1) direct uptake of DNA or DNA-containing particles by the cell, (2) cell fusion with other cells or ghost cells, (3) microinjection, and (4) infective transformation. A fifth method is being developed which involves the use of accelerated high-velocity one-micron-sized particles for the purpose of carrying DNA into cells and tissues.

Uptake mechanisms include the following: (1) induction of enhanced membrane permeability by use of $Ca^{++}$ and temperature shock (Mandel and Higa, 1970; Dityakin et al., 1972); (2) use of surface binding agents such as PEG (Chang and Cohen, 1979; Krens et al., 1982) or $Ca(PO_4)_2$ (Graham and van der Eb, 1973; Wiglet et al., 1979); and (3) phagocytosis of particles such as liposomes (Uchimaya et al., 1982), organelles (Potrykus, 1973), or bacteria (Cocking, 1972), into the cell. These uptake mechanisms generally involve suspensions of single cells, where any existing cell wall materials have been removed enzymatically. Uptake protocols are generally quite simple and allow treatment of large numbers of cells en masse. In such systems most cells are unaffected, but cell selection procedures are available to recover the rare cells that have been transformed (Powers and Cocking, 1977).

Fusion mechanisms incorporate new genetic material into a cell by allowing it to fuse with another cell. A variation on this theme involves ghost cells. The membrane of killed cells are allowed to fill with a given DNA solution, such that cell fusion incorporates the DNA from the carrier "cell" into the living cell. Cell-to-cell fusion can be induced with the aid of such things as PEG (Bajaj, 1982) and Sendai virus particles (Uchida et al., 1980). As with uptake mechanisms, fusion technologies rely upon the use of single cell suspensions, where cells are enzymatically stripped of any cell wall material. While fusion technologies can have relatively good efficiencies in terms of numbers of cells affected, the problems of cell selection can be more complex, and the resulting cells are typically of elevated ploidy.

Microinjection technologies employ extremely fine, drawn out capillary tubes, which are called microelectrodes. These can be made sufficiently small that they can be used as syringe needles for the direct injection of biological substances into certain types of individual cells (Diacumakos, 1973; Graessmann and Graessmann, 1983). One modification of microinjection involves pricking with a solid-glass drawn needle, which carries in biological solutions which are bathing the cell (Yamomoto et al., 1981). Another modification is called ionophoresis (Purres, 1981; Ocho et al, 1981), which uses electrophoresis of substances out of the microelectrode and into the cell as an alternative to high pressure bulk flow. Microinjection procedures can give extremely high efficiencies relative to delivery into the cell. Because of this, microinjection has been used successfully in the transformation of individual egg cells.

In another example, foreign DNA was successfully injected into cotton pollen tubes without the pollen being damaged or its germination being inhibited. Although this involved a resistance gene from another plant instead of a parasite gene, the same technique can be used in the practice of the present invention. DNA was injected into the nucleus of cotton pollen grains germinating on cellophane using micro-manipulators and a micro-injection system. This operation was carried out on the fixed stage of an inverted research microscope equipped with Nomarski differential interference optics. Foreign DNA in a recipient nucleus was detected by epifluorescence after the incorporation of a fluorescent marker in the injected material. The DNA was introduced using "quickfill" tubing drawn to a tip diameter of 0.5 micron, and the DNA was injected into the nucleus iontophoretically. The germinating pollen was returned to the style where it continued to grow and fertilize the ovule. About 2N injections can be carried out per day. Seeds from the micro-injected plants were planted, and seedlings were raised and screened. Screening may be carried out by testing for the presence of the foreign gene by Southern blotting or for the presence of the gene product by means of enzyme inhibition assays. In addition, screening for insect resistance of the developing square and boll can be utilized when cotton is the host. Other plants can be treated in the same manner.

Infective transformation employs non-injurious infective agents of the host, such as viruses, which naturally transmit part of their genome into the host. In plants, the principal mode of transformation now being practiced is the use of the infective agent *Agrobacterium tumefaciens*. This bacterium will naturally colonize cells of any dicotyledonous plant and transmit a specific "T-region" of its Ti-plasmid into the plant chromosome. Other plant vectors useful for the transformation of plants can similarly be used. Genes of interest can now be routinely engineered into the T-region and can be transmitted to the plant by the bacterium (see Fraley et al., 1983). Simple conincubation (growing plant cells and bacterial cells together) has been shown to be extremely effective in transforming plant protoplasts and leaf disks, and whole transformed plants have now been regenerated in numerous plant species (see Horsch et al., 1984). In mammals, naturally infective retroviruses have been used to construct naturally transforming vectors which insert engineered DNA into the mammalian chromosome, in a manner similar to *Agrobacterium tumefaciens*. This transformation mechanism is considered extremely promising for animal and human gene therapy (see Anderson, 1984).

For an example of mammalian transformation, see U.S. Pat. No. 4,396,601 to Salser et al., which describes a technique in which cells are isolated from a regenerative body member of a mammal or a syngeneic equivalent to provide parent cells. The parent cells are combined with DNA from the parasite and with additional DNA that produces a a selection advantage over the parent cells when the cells are subjected to mitotic inhibition. The modified cells are then introduced into the host in a manner such that the modified cells return to the body member from which the parent cells were obtained. A mitotic inhibitor is then administered to the host to provide a selective advantage for the modified cells over the parent cells, thereby regenerating the modified cells in the host. Further details of this method can be obtained by reference to U.S. Pat. No. 4,396,601.

The method of the invention is generally applicable to the protection of any host from a parasite of that host. As used herein, "host" refers to any organism that can be infected by any parasitic or symbiotic organism. The term "parasite" refers to any organism that obtains substance or means for reproduction from an organism, whether it lives with that organism in a parasitic or symbiotic relationship. The parasite need not be specific for a particular host but may be a parasite of many hosts, such as the caterpillars of numerous moths and bufferflies. Although a preferable parasite for use in this invention is a virus, whether the virus is a DNA or RNA virus, other parasites are also encompassed by this term. Examples of other parasites include bacteria, protozoa, fungi, nemotodes, insects, and arachnids.

Since a host is normally higher in the evolutionary scheme than the parasite, the term "host" does not encompass a virus, which resides at the bottom of the evolutionary scheme. However, any higher organism is capable of being infected by a parasite. The invention is readily applicable, for example, to bacteria grown in culture which need protection against infection from bacteriophages. Additionally, plants and other higher organisms, such as mammals, also can be readily protected from viruses using the method of the invention. Both plants and animals can also be protected from higher parasitic hosts, such as insects and protozoans, subject to the restrictions which have already been discussed. Examples of hosts include bacteria, yeasts, lungi (e.g., mushrooms), legumious plants (e.g., soybeans), cereal and forage crops (e.g., corn, wheat, rice and alfalfa), food crops (e.g., tomatoes, potatoes, lettuce, and onions), ornamental plants (e.g., roses, junipers, and orchids), trees (e.g., pine, spruce, and walnut), protozoans amphibians, reptiles, birds (e.g., chickens and turkeys), and mammals (e.g., cats, dogs, horses, cattle, sheep, goats, pigs, and primates).

Examples of host/parasite systems in which either the host or the parasite is a unicellular organism (the most common situations) can be found in numerous microbiology textbooks and reference manuals, such as CRC Handbook of Microbiology, Condensed Edition, Laskin and Lechevalier (eds.), CRC Press, Cleveland, Ohio, 1974. Other examples of host/parasite systems are given below along with examples of how resistance to the parasite can be given to the host in that system. These examples are not limiting, and many other methods for achieving resistance are possible for each listed system.

1) There are a variety of bacteria important in industrial fermentation processes, such as *Streptococcus lactis, Streptococens cremoris,* and *Lactobacillus species.* During fermentation, infection by various bacteriophages is a common cause of fermentation failure. Bacterial resistance to such bacteriophage infection can be engineered by methods exactly analogous to the methods described above for engineering resistance to the Qβ bacteriophage in *E. coli.*

2) There are hundreds of significant plant RNA viruses, and essentially all crop species are affected by one or more such viruses. Resistance to such viruses can be obtained in a manner closely analogous to Qβ resistance in bacteria, by cloning fragments of the viruses into plant-transforming vectors such as a modified Ti-plasmid and transforming the appropriate plants. Plants transformed by various gene fragments can then be screened for resistance, using established plant breeding techniques. A few relevant viruses include alfalfa mosaic virus, brome mosaic virus, barley yellow dwarf virus, beet yellows virus, cucumber mosaic virus, lettuce necrotic yellows virus, maize chlorotic dwarf virus, pea enation virus, potato viruses S, X, and Y, southern bean mosaic virus, tomato ringspot virus, tobacco ringspot virus, tobacco mosaic virus, tobacco streak virus, turnip yellow mosaic virus, and wound tumor virus.

3) There are certain animal and human pathogens, such as the flu and common cold viruses, which have evolved mechanisms for circumventing the effectiveness of the animal immune system. Where such a virus is a chronic problem, as with flu and colds, parasite-derived resistance will be a powerful tool for conferring immunity to all strains of that pathogen. Resistance can be engineered by cloning fragments of the viral genome, introducing the gene fragments into animal cells in vitro by use of retrovital vectors, testing of varius tranformed cell times to determine which have conferred resistance to infection by the virus, and then using those fragments conferring resistance to create benign non-infectious retrovirus vectors for the purpose of introducing resistance genes into individuals.

4) There are certain retroviruses which attack T-cells (i.e., the human immune system) directly (such as the viruses that produce AIDS), thereby circumventing our natural immune defense mechanism. Resistance can be engineered as described above, using AIDS genomic fragments, and also using AIDS, or a similar retrovirus, for the construction of a T-cell-specific transforming vector. Transformed T-cells with resistance-conferring fragments of the AIDS genome would have a selective advantage over other susceptible T-cells, becoming the predominant form of T-cell and thereby giving rise to resistant individuals.

5) A wide range of bacteria and fungi that parasitize plants have intimate contact with living host cells and reveal gene-for-gene host parasite relations. Resistance in such cases can be engineered by cloning avirulence alleles from avirulent strains of the parasite and introducing these genes into the relevant host for the purpose of conferring resistance. A few pathogens where this method is relevant include *Puccinia sorghi* infection of corn, Puccinia infections of wheat, *Phytophthora infestans* infection of potato, Ustilago infection of rye, and *Melampsora lini* infection of flax.

6) A wide range of insects parasitize plants, causing severe economic losses, and depend upon a proper balance of juvenile hormone and molting hormone to regulate their development. Therefore, broad-spectrum, insect-derived plant resistance to insects can be engineered by cloning the insect genes responsible for the final steps of the biosynthesis of these hormones and transferring these genes to the plant hosts of interest, using established transformation techniques. Typical genes would code for enzymes controlling the conversion of a precursor into the desired regulatory product (e.g., hormone). Basically all plant hosts contain the precursors for the synthesis of these hormones; i.e., famesol in the case of juvenile hormone and phytosterols in the case of molting hormone. Other useful genes would be those producing other regulatory substances that trigger the production of hormones in parasites. A few insect parasites which could be controlled by this method include flea beetles, wire worms, cutworms, grubs, aphids, leafhoppers, tarnished plant bugs, Colorado potato beetles, cucumber beetles, weevils, cabbage worm, cabbage lopper, leafminers, Hessian fly, grasshopper, tent worm, gypsy moth, tussock moth, army worm, corn ear worm, European corn borer, and Japanese beetle.

7) A wide range of insects parasitize plants and contain neurotransmitters which control essential body functions. Such neurotransmitters are oligopeptides typically only 5–20 amino acids long. In this case insect-derived resistance can be engineered by sequencing the oligopeptide and synthesizing artificial genes homologous to the native insect genes coding for these neurotransmitters. These synthetic genes, when expressed in a plant host, can then disrupt that crucial body function normally regulated by that neurotransmitter of the insect parasite. The insect listed in the previous example would be equally valid as candidates for this method of deriving parasite-derived resistance.

In addition to the above general procedures which can be used for preparing recombinant DNA molecules and transformed unicellular organisms in accordance with the practices of this invention, other known techniques and modifications thereof can be used in carrying out the practice of the invention. In particular, techniques relating to genetic engineering have recently undergone explosive growth and development. Many recent U.S. patents disclose plasmids, genetically engineered microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified to the practice of the invention described in this specification by those skilled in the art of genetic engineering.

All of the patents and other publications cited in this specification are indicative of the level of skill and knowledge of those skilled in the arts to which the present invention pertains. All publications, whether patents or otherwise, referred to previously or later in this specification are herein separately incorporated by reference. Although full incorporation of the individual publications is intended, it is recognized that those of ordinary skill in the art can readily determine from the incorporated publications those sections which are most relevant to the present invention and those sections which could be deleted without loss of understanding.

In addition to the method of producing resistance to a parasite described above in detail, this invention also encompasses hosts produced by the process of the invention as well as recombinant vectors and other products of genetic engineering useful in the practice of the invention.

The invention now being generally described, the same will be better understood by reference to certain specific examples which are included herein for purposes of illustration only and are not intended to be limiting of the invention or any embodiment thereof, unless so specified.

EXAMPLE

The feasibility of the concept outlined above was proven with experiments using the bacteriophage Qβ and its host, *E. coli*. Using cDNA clones of Qβ (Qβ is an RNA phage), plasmids were first constructed or obtained which would express part of the Qβ cDNA in *E. coli* and confer resistance.

Coat Protein: The plasmid used for production of the coat protein was pGL101 obtained from R. B. Winter (Cell 33, 877). This plasmid expresses the coat protein under lac operator control, so its expression can be induced by IPTG (though there is also a constitutive expression). This plasmid as well as the others described below contain the gene encoding amp$^r$.

Negative Strand: A plasmid was constructed that inserted the 0.9 Kb HpaII fragment of Qβ cDNA into pUR222 plasmid at the AccI site. This fragment extends from positions 2547 to 3473 in Qβ (FIGURE) and includes translational sequences of the replicase gene. These sequences also contain the M-binding site of the replicase. In the "sense" orientation of this fragment, a fusion product between β-galactosidase protein and the replicase fragment is formed. In the antisense (reverse) ligation of this fragment, an RNA complementary to the Qβ RNA sequence is formed. Both constructions were made.

Testing for Resistance: The strain GM1 (provided by R. W. Webster) was transformed with pUR222 or one of the test plasmids described above. These strains were grown up, made competent, incubated with Qβ and then plated out in soft agar. Plaque numbers and sizes were assessed to determine if resistance was taking place.

In an initial experiment to test the coat protein, GM1+pUR227. and GN1+pGL101 were grown in 10 mls L-broth containing ampicillin in IPTG. At stationary phase the cultures were pelleted and resuspended in 4 ml 50 mM YCaCl$_2$. A small portion, 0.1 ml, of this plating culture was incubated 60' with $10^7$ pfu of Qβ. This was then plated on YT-ANP plates in 3 ml soft agar with IPIG. The results were that the GM1+pUR222 plates had thousands of plaques which soon (24 hrs) engulfed the plate; the GN1+pGL101 plate at first showed no plaques but later developed many very small plaques.

To check the possibility that the GM1 strain+pGL101 resistance was due to loss of the F' element, the strains were subsequently grown on minimal medium lacking proline to maintain selection for the F'. The same protocol as above was then repeated, including strains of GN1 with the HpaII (sense) and HpaII (antisense) bearing plasmids. The results are presented in Table 1. Both the coat protein and the HpaII (antisense) plasmids could confer resistance to Qβ infection. This experiment was repeated twice with essentially the same results. After continued passage, however, the plasmid bearing Qβ cDNA sequences rearranged or were lost. Additionally, the pGL101 was tested at higher titer ($10^{11}$ pfu); it still conferred resistance. Coat-conferred resistance from the RNA phages f1 and f2 were tested. GN1 with pGL101 was resistant to f2 but not f1 as might be expected considering their modes of infection.

TABLE 1

| Strain + Plasmid | Inducer | # of Plaques | Size |
|---|---|---|---|
| GM1 — | + | 300 | normal |
| puR222 | − | 360 | " |
| " | + | 348 | " |
| Hpa (antisense) | − | 247 | " |
| " | + | 263 | small |
| Hpa (sense) | − | 224 | normal |
| " | + | 234 | " |
| pGL101 | − | 176 | very small |
| " | + | 101 | very very small |

Replicase Binding Domain

In an experiment similar to those described above, a model system involving *E. Coli* and its viral pathogen Qβ was utilized. A pBR322 plasmid containing a cDNA clone from the 3' end of the Qβ genome was obtained from Martin Billeter at the University of Zurich. The gene segment of this plasmid encodes all of the replicase gene of Qβ. Various DNA constructions were made using this source of a gene encoding the Qβ viral replicase. The constructs were made by annealing a 5' Sau3a site in the replicase coding region to a BamHI site in the lacZ gene on the pUC18 plasmid. The pUC18 plasmid is commercially available from Bethesda Research Laboratories. The restriction enzymes used in producing the fragments as well as various other enzyme used in the genetic engineering steps described herein are also commercially available.

This process created a gene, when in-frame, encoding a few amino-terminal amino acids of lacZ followed by a replicase protein domain terminating with a NarI site beyond the transcriptional termination site of the replicase enzyme. Since the restriction enzyme Sau3a recognizes a large number (approximately 8) of cleavage sites in the replicase gene, a number of different DNA constructs were produced. The plasmids produced in this manner resulted in the production of the replicase domain being under lacZ promoter control. Some of the Sau3a sites in the replicase gene produced an out-of-frame fusion of replicase.

The vector constructions so made were transformed into E. Coli JM103, a commercially available strain. The size of the replicase gene fragment in each construction was determined, and the susceptibility of each transformant to Qβ infection was tested.

Basically, there were two classes of fusions. One class contained approximately 1,000 base pairs of the 3' end of the replicase (4 out of 5 should be in-frame) and one class contained approximately 500 base pairs of the 3' end (2 of 3 would be out-of-frame). The 1,000-BP class was represented by clones #7, #10 and 19011, while the 500-BP class was represented by #4, #5, and #8 (see FIGURE). The colonies containing these constructions were grown in L-broth and then in M-9 media to select for male E. coli. Both of these media are commercially available and are described in Maniatis et al, *Molecular Cloning, A Laboratory Manual*, Cold Spring Harbor Laboratories, Cold Spring Harbor, N.Y. (1982). A plating culture was then made either with or without IPTG-induction (IPTG is isopropyl thiogalactoside). It was initially suspected that induction of lacZ expression with IPTG would be needed to produce enough replicase protein fragment in order to see protection from infection. However, as shown below, this did not prove to be necessary.

The results of the comparative tests are seen in Table 1 below. Plasmid pUC9 is JM103 with the parental plasmid which served as a negative control. The reference 2290 is to the original whole-replicase-containing plasmid in JM103. All of the replicase fusion products produced a 10-fold or more protection against infection except construction #8. This construction had the smallest portion of the replicase gene and may not be in-frame. All of the strains were about equally infectable as determined by infection with a different pilus-specific phage, f2.

TABLE I

| | No. of plaques/plate | | |
|---|---|---|---|
| Strain with Plasmid | −IPTG | +IPTG | f2 |
| PUC9 | 240 | 2400 | 172 |
| 2290 | 294 | 600 | 116 |
| #7 | 250 | 87 | 332 |

TABLE I-continued

| | | No. of plaques/plate | | |
|---|---|---|---|---|
| | Strain with Plasmid | −IPTG | +IPTG | f2 |
| 1000 bp | #10 | 166 | 53 | 348 |
| | #11 | 264 | 16 | 279 |
| | #4 | 243 | 36 | 277 |
| 500 bp | #5 | 208 | 144 | 266 |
| | #8 | 240 | 1342 | 215 |

The results set forth above indicate that bacteria (and by inference other hosts) can be protected against infection with an RNA virus by inserting a gene controlling production of an inoperative fragment of a viral RNA replicase enzyme into a host organism.

The invention now being fully described, it will be apparent to one of ordinary skill in the art that many changes and modifications can be made thereto without departing from the spirit or scope of the invention as set forth herein.

REFERENCES CITED

Ames, B. N. (1983). *Science* 221: 1256–1264.
Anderson, W. F. (1984). *Science* 226: 410–409.
Bajaj, Y. P. S. (1982) In: Reinert, J. and Bajaj, Y. P. S. (eds.), *Plant Cell, Tissue and Organ Culture*. Springer-Verlag, New York, pp. 467–496.
Baserga, R., C. Crose, G. Rovera, Eds. (1980). Introduction of macromolecules into viable mammalian cells. In: *Sinstar Symposium Series VI*. A. R. Liss Inc. New York.
Bernardi, A. and Spahr, P. (1972). *Proc. Nat. Acad. Sci.* 69: 3033.
Bowers, W. S. (1980). In: *Insect Biology in the Future* p. 613. New York, Academic Press.
Chang, S. and Cohen, S. N. (1979). *Mol. Gen. Genet.* 168: 111–115.
Cocking, E. C. (1972). *Ann. Rev. Plant Physiol.* 23: 29–50.
Diacumakos, E. G. (1973). In: Prescott, D. M. (ed.), *Methods in Cell Biology*. Academic Press, New York, pp. 287–311.
Dityatkin, S. Y., Lisovskaya, K. V., Panzhava, N. N., Iliashenko, B. N. (1979). *Biochimica et Biophysica Acta* 281: 319–323.
Dorssers, L., Meet, J. van der, Kammen, A. van, and Zabel, P. (1983). *Virology* 125: 155–174.
Fairfield, A. S., S. R. Meshnick, and J. W. Eaton. (1983). *Science* 221: 764–766.
Flashman, S. F. (1978). *Mol. Gen. Genet.* 166: 61–73.
Flor, H. H. (1971). *Ann. Rev. Phytopathol.* 9: 27S–296.
Fraley, R. T., et al. (1983). *Proc. Natl. Acad. Sci.* 80: 4803–4807.
Gibbs, A. (1969). *Adv. Virus Res.* 14: 263–327.
Graessmann, M. and Graessmann, A. (1983). *Methods in Enzymology* 101: 482–492.
Graham, F. L. and van der Eb, A. J. (1973). *Virology* 52: 456.
Hall, T. C., W. A. Miller, and J. J. Bujarski. (1982). In: *Advances in Plant Pathology*. P. 179. (vol. 1) Academic Press, New York.
Hamilton, R. I. (1980). In: *Viruses. Plant Disease: An Advanced Treatise.* P. 279. (Vol. 5). Academic Press, N.Y.
Held, G. A., L. A. Bulla, E. Ferari, J. Hoch, A. I. Aronson, and S. A. Minnich (1982). *Prov. Natl. Acad. Sci.* 79: 6065–6069.
Horsch, R. B., R. T. Fraley, S. G. Rogers, P. R. Sanders, A. Lloyd, N. Hoffmann (1984). *Science* 223: 496–498.
Izant, J. and Weintraub, H. (1984). *Cell* 36: 1007–1015.

Kamen, G. and P. Argos (1984). *Nucleic Acids Res.* 12: 7269.

Kamen, R. (1970). *Nature* 228: 527–553.

Karnik, S. and Billeter, M. A. (1983). *EMBO* 2: 1521.

Krens, F. A., Molendijk, L., Wullems, G. J., and Schilperoort, R. A. (1982). *Nature* 296: 72.

Mandel, M. and Higa, A. (1970). *J. Mol. Biol.* 53: 159–162.

Marcus, P. I. and Carrier, D. H. (1967). *J. Virology* 1: 334.

Marcus, P. I. and Zuckerbraun, H. L. (1969). In: *The Biology of Large RNA Viruses.* P. 455. Acad. Press, New York.

Marcus, P. I. and Zuckerbraun, H. L. (1970). *Ann N.Y. Acad. Sci.* 173: 185–198.

Meyer, F., H. Weber, and C. Weissmann. (1976). *Experientia* 32: 804.

Meyer, F., Weber, H. and Weissman, C. (1981). *J. Mol. Biol.* 153: 631–660.

Mizuno, T., Chou, M. and Inouye, M. (1984). *Proc. Natl. Acad. Sci. U.S.A.* 81: 1966–1970.

Mouches, C., Candresse, T. and Bove, J. M. (1984). *Virology* 134: 78–90.

Ocho, M., Nakai, S., Tasaka, K., Watanabe, S., and Oda, T. (1981). *Acta Ned. Okayarea* 35 (5): 381–384.

Potrykus, I. (1973). *Z. Pflanzenphysiol.* 70: 364–366.

Power, J. B. and Cocking, E. C. (1977). In: Reinhert, J., and Bajaj Y. P. S. (eds.) *Plant Cell, Tissue and Organ Culture.* Springer-Verlag, New York, pp. 497–505.

Purres, R. D. (1981). Academic Press, New York, 146 p.

Roberts, T. M., Kacich, R. and Ptashne, M. (1979). *Proc. Natl. Acad. Sci. U.S.A.* 76: 760–764.

Silverman, P. M., Rosenthal, S., Mobach, H., and Valentine, R. C. (1968). *Virology* 36: 142.

Staskawicz, A. J., D. Dahlbeck, and N. Keen (1984). *Proc. Natl. Acad. Sci. U.S.A.* 81: 6024.

Uchida, T., Yamaizumi, N., Nakada, E., Okada, Y. (1980). In: *Introduction of macromolecules into viable mammalian cells.* Windsor Symposium Series VI, A.R. Liss Inc., New York, pp. 169–185.

Uchimiya, H., Ohgawara, T., and Harada, H. (1982). In: Fujiwara A. (ed.), *Proc. 5th Intl. Cong. Plant Tissue and Cell Culture,* Jap. Assoc. for Plant Tissue Culture. Tokyo. pp. 507–508.

Van der Plank, J. E. (1978). *Genetic and Molecular Basis of Plant Pathogenesis.* Springer-Verlag, N.Y. pp. 167.

Wigler, M., Sweet, R., Sim, G. K., Wold, B., Pellicer, A., Lacy, E., Maniatis, T., Silverstein, S., and Axel, R. (1979). *Cell* 16: 777.

Winter, R. B. and Gold, L. (1983). *Cell* 33: 877–855.

Yamamoto, F., Furusawa, M., Furusawa, I., and Obinata, M. (1982). *Exp. Cell Res.* 142: 79–84.

Zinder, N. D. (ed) (1975). *RNA Phages.* Cold Springs Harbor Laboratory, N.Y. pp. 428.

Barton, K. A., and Brill, W. J. (1983). *Science* 219: 671–676.

Illmensee, W. (ed.) (1984). Long Term Goals in Agricultural Plant Improvement. Genetic Manipulation—Impact on Man and Society. Cambridge Univ. Press.

Day, P. R., Barrett, J. A., and Wolfe, M. S. (1983). Evolution of host-parasite interaction. In: Genetic Engineering of Plants: An Agricultural Perspective. Kosuge, P., Meredith, C. P., and Hollaender, A., eds. Plenum Press, New York.

What is claimed as new and desired to be secured by Letters Patent of the United States is:

1. A method of making bacterial cells resistant to infection by a virus, comprising:
    a) isolating DNA coding for a gene, or fragment thereof, of said virus;
    b) operably linking said DNA, or a fragment thereof, within an expression vector;
    c) transforming said bacterial cells with said expression vector;
    d) culturing said transformed bacterial cells in the presence of said virus, wherein said DNA, or fragment thereof, is expressed as a gene product, and wherein said gene product disrupts an essential activity of said virus; and
    e) identifying said transformed bacterial cells which are resistant to infection by said virus by selecting said transformed bacterial cells which survive or resist infection by said virus.

2. The method of claim 1, wherein said transformed bacterial cells comprise plasmids containing said DNA, or fragment thereof, wherein said plasmids are capable of replication in said transformed bacterial cells.

3. The method of claim 1, wherein said DNA, or fragment thereof, is inserted into the chromosomes of said bacterial cells.

4. The method of claim 1, wherein said bacterial cells are selected from the group consisting of bacterial cells of the genera Escherichia, Streptococcus, Streptococens and Lactobacillus.

5. The method of claim 4, wherein said bacterial cells are selected from the group consisting of *Escherichia coli, Streptococcus lactis* and *Streptococens cremoris.*

6. The method of claim 1, wherein said DNA is cDNA.

7. The method of claim 1, wherein said gene, or fragment thereof, is selected from the group consisting of a replicase gene or fragment thereof, a coat protein gene or fragment thereof, and a maturation protein gene or fragment thereof.

8. The method of claim 7, wherein said gene or fragment thereof is a replicase gene fragment.

9. The method of claim 8, wherein said gene or fragment thereof contains a binding site for a replicase enzyme.

10. The method of claim 7, wherein said gene or fragment thereof is a coat protein, maturation protein, or a fragment thereof.

11. A method of making cultured plant cells or cultured plant tissue resistant to infection by an RNA virus, comprising:
    a) isolating DNA coding for a gene, or fragment thereof, of said virus;
    b) operably linking said DNA, or a fragment thereof, within an expression vector;
    c) transforming said plant cells or plant tissue with said expression vector;
    d) growing said transformed plant cells or plant tissue in the presence of said virus, wherein said DNA, or fragment thereof, is expressed as a gene product, and wherein said gene product disrupts an essential activity of said virus; and
    e) identifying said transformed plant cells or plant tissue which are resistant to infection by said virus by selecting said transformed plant cells or plant tissue which survive or resist infection by said virus.

12. The method of claim 11, wherein said DNA or fragment thereof is expressed in the sense direction.

13. The method of claim 11, wherein said DNA or fragment thereof is expressed in the antisense direction.

14. The method of claim 11, wherein said gene or fragment thereof is a replicase gene or fragment thereof.

15. The method of claim 14, wherein said gene or fragment thereof contains a binding site for a replicase enzyme.

16. The method of claim 11, wherein said plant cells or plant tissue are dicotyledonous.

17. The method of claim 11, wherein said expression vector is an *Agrobacterium tumefaciens* plasmid.

18. The method of claim 11, wherein said virus is selected from the group consisting of alfalfa mosaic virus, brome mosaic virus, barley yellow dwarf virus, beet yellows virus, cucumber mosaic virus, lettuce necrotic yellow virus, maize chlorotic dwarf virus, pea enation virus, potato virus S, potato virus X, potato virus Y, southern bean mosaic virus, tomato ringspot virus, tobacco ringspot virus, tobacco mosaic virus, tobacco streak virus, turnip yellow mosaic virus and wound tumor virus.

19. The method of claim 18, wherein said virus is selected from the group consisting of tobacco mosaic virus, cucumber mosaic virus, alfalfa mosaic virus and tobacco ring spot virus.

20. The method of claim 11, wherein said plant cells or plant tissue are tomato cells or tissue.

21. The method of claim 11, wherein said plant cells or plant tissue are cotton cells or tissue.

22. The method of claim 18, wherein said plant cells or plant tissue are potato cells or tissue and said virus is potato virus X.

23. The method of claim 18, wherein said plant cells or plant tissue are potato cells or tissue and said virus is potato virus Y.

24. The method of claim 11, wherein said gene or fragment thereof is a coat protein gene or a fragment thereof.

25. The method of claim 16, wherein said expression vector is an *Agrobacterium tumefaciens* plasmid.

26. The method of claim 25, wherein said virus is selected from the group consisting of alfalfa mosaic virus, brome mosaic virus, barley yellow dwarf virus, beet yellows virus, cucumber mosaic virus, lettuce necrotic yellow virus, maize chlorotic dwarf virus, pea enation Virus, potato virus S, potato virus X, potato virus Y, southern bean mosaic virus, tomato ring spot virus, tobacco ring spot virus, tobacco mosaic virus, tobacco streak virus, turnip yellow mosaic virus and wound tumor virus.

27. The method of claim 26, wherein said virus is selected from the group consisting of tobacco mosaic virus, cucumber mosaic virus, alfalfa mosaic virus and tobacco ring spot virus.

28. The method of claim 16, wherein said plant cells or plant tissue are tomato, cotton or potato cells or tissue.

* * * * *

UNITED STATES PATENT AND TRADEMARK OFFICE
CERTIFICATE OF CORRECTION

PATENT NO. : 5,580,716
DATED : December 3, 1996
INVENTOR(S) : Johnston, et al.

It is certified that error appears in the above-identified patent and that said Letters Patent is hereby corrected as shown below:

Column 1, line 20, "vital" should read --viral--.

Column 3, line 49, "a vital function" should read --a viral function--.

Column 3, line 52, "vital" should read --viral--.

Column 6, line 56, "interlet" should read --interfere--.

Column 7, line 18, "vital" should read --viral--.
Column 7, line 24, "vital" should read --viral--.
Column 7, line 54, "vital" should read --viral--.
Column 7, line 56, "vital" should read --viral--.
Column 7, line 61, "vital" should read --viral--.
Column 7, line 63, "vital" should read --viral--.

UNITED STATES PATENT AND TRADEMARK OFFICE
CERTIFICATE OF CORRECTION

PATENT NO. : 5,580,716

DATED : December 3, 1996

INVENTOR(S) : Johnston, et al.

It is certified that error appears in the above-identified patent and that said Letters Patent is hereby corrected as shown below:

Column 8, line 19, "vital" should read --viral--.

Column 8, line 21, "vital" should read --viral--.

Column 11, line 12, "that those of" should read --by those of--.

Column 13, line 18, "Wiglet et al." should read --Wigler et al.--.

Column 15, line 15, "lungi" should read --fungi--.

Column 16, line 1, "varius" should read --various--.

Column 16, line 40, "famesol" should read --farnesol--.

UNITED STATES PATENT AND TRADEMARK OFFICE
CERTIFICATE OF CORRECTION

PATENT NO. : 5,580,716
DATED : December 3, 1996
INVENTOR(S) : Johnston, et al.

It is certified that error appears in the above-identified patent and that said Letters Patent is hereby corrected as shown below:

Column 18, line 24, "pUR227" should read --pUR222--.

Column 18, line 44, "rearranged"
        should read --were rearranged--.

Column 19, line 35, "#10 and 19011"
        should read --#10 and #11--.

Signed and Sealed this

Twenty-ninth Day of May, 2001

Attest:

NICHOLAS P. GODICI

*Attesting Officer*     *Acting Director of the United States Patent and Trademark Office*